US008591980B2

(12) United States Patent
Markosyan et al.

(10) Patent No.: US 8,591,980 B2
(45) Date of Patent: *Nov. 26, 2013

(54) LOW CALORIE COMPOSITE SWEETENER AS SUGAR ALTERNATIVE AND METHODS FOR PRODUCING THE SAME

(71) Applicants: Avetik Markosyan, Kuala Lumpur (MY); Siddhartha Purkayastha, Lombard, IL (US)

(72) Inventors: Avetik Markosyan, Kuala Lumpur (MY); Siddhartha Purkayastha, Lombard, IL (US)

(73) Assignee: PureCircle Sdn Bhd, Negeri Sembilan (MY)

( * ) Notice: Subject to any disclaimer, the term of this patent is extended or adjusted under 35 U.S.C. 154(b) by 0 days.

This patent is subject to a terminal disclaimer.

(21) Appl. No.: 13/684,255

(22) Filed: Nov. 23, 2012

(65) Prior Publication Data
US 2013/0084317 A1    Apr. 4, 2013

Related U.S. Application Data

(62) Division of application No. 12/750,720, filed on Mar. 31, 2010, now Pat. No. 8,357,417.

(51) Int. Cl.
*A23L 1/236* (2006.01)

(52) U.S. Cl.
USPC .............................. 426/548; 426/89; 426/103

(58) Field of Classification Search
USPC ..................... 426/89, 103, 285, 471, 548, 658
See application file for complete search history.

(56) References Cited

U.S. PATENT DOCUMENTS

| | | | |
|---|---|---|---|
| 1,902,773 A | 3/1933 | Hale | |
| 3,293,133 A | 12/1966 | Hill et al. | |
| 3,619,294 A | 11/1971 | Black et al. | |
| 5,401,519 A | 3/1995 | Sabase et al. | |
| 5,779,805 A | 7/1998 | Morano | |
| 6,214,402 B1 | 4/2001 | Fotos et al. | |
| 6,703,057 B2 | 3/2004 | Duffett | |
| 8,334,006 B2 * | 12/2012 | Purkayastha et al. | 426/548 |
| 8,357,417 B2 * | 1/2013 | Markosyan et al. | 426/548 |
| 2008/0292775 A1 | 11/2008 | Prakash et al. | |
| 2010/0034945 A1 | 2/2010 | Arango Moreno | |

FOREIGN PATENT DOCUMENTS

| | | |
|---|---|---|
| EP | 0334617 A2 | 9/1989 |
| GB | 1566821 | 5/1980 |
| JP | 358020170 A | 2/1983 |

* cited by examiner

*Primary Examiner* — Leslie Wong
(74) *Attorney, Agent, or Firm* — Pyprus Pte Ltd

(57) ABSTRACT

The invention provides a process for producing a low calorie composite sweetener as a sugar alternative. The invention further provides a low calorie composite sweetener that can be used in many products. The low calorie composite sweetener is useful as non-caloric sweeteners in edible and chewable compositions such as any beverages, confectionaries, bakeries, cookies, chewing gums, and alike.

6 Claims, 2 Drawing Sheets

LOW CALORIE COMPOSITE SWEETENER AS SUGAR ALTERNATIVE AND METHODS FOR PRODUCING THE SAME

CROSS REFERENCE TO RELATED APPLICATION

This application is a divisional application of U.S. patent application Ser. No. 12/750,720 filed Mar. 31, 2010 now U.S. Pat. No. 8,357,417.

FIELD OF THE INVENTION

The invention relates to natural sweeteners, and more particularly to a low caloric composite sweetener as a sugar alternative comprising a blend of sugar and natural high intensity sweetener and further to a method for producing the low calorie composite sweetener.

BACKGROUND OF THE INVENTION

Sugar-high intensity sweetener blends have been formulated to produce low calorie composite sweeteners, being used as sugar alternatives with reduced calorific values. Aside from having lower calorific value, it is important that the low calorie composite sweetener as a sugar alternative shall have similar appearance, taste profile, bulk properties and heat resistance as sucrose. For example, the similar appearance would enable a sugar alternative to have a decorative function in addition to sweetening and bulking properties; the heat resistance is essential for a large number of food and beverage applications that operate at high temperature; otherwise a sugar alternative with low heat resistance tends to degrade when subjected to heat.

Various methods for production of such blends have been developed to produce low calorie sweetener compositions.

U.S. Pat. No. 6,214,402 describes a co-crystallization process between sugar and N-{N-(3,3-dimethylbutyl)-L-alpha-aspartyl}-L-phenylalanine 1-methylester. It comprises the steps of mixing sugar with water, heating the mixture to 120° C., then seeding the mixture with a pre-mixture comprising N-{N-(3,3-dimethylbutyl)-L-alpha-aspartyl}-L-phenylalanine 1-methylester and sugar, followed by allowing the resulted mixture to cool at intensive stirring conditions. It is to be noted that the process was carried out under normal atmospheric pressure conditions, and high temperatures, particularly 120° C. In this case, darkening of mixture promoted by high temperature might occur which in turn affects the color and appearance of the final product. Another drawback of the method is the high power consumption of employed processes.

US Patent Application 2010/0034945 describes a process of preparation of co-crystallized product comprising sugar and a natural sweetener. The product is prepared by co-crystallizing sucrose and a natural sweetener in a vacuum pan under controlled pressure and temperature conditions followed by separating the crystal from the "sugar juice". The drawback of this process when it is employed for co-crystallization of sugar and high intensity sweetener is the difficulty of controlling the ratio of sugar and high intensity sweetener in the final crystals. The distribution of high intensity sweetener between two phases (crystals and "sugar juice") can have significant variance which, in case of high sweetness power of aforementioned sweeteners will result in substantial batch to batch variability of sweetness level of final product. Besides, in order to prevent loss of high intensity sweetener which remains in liquid phase, additional recovery/recirculation steps are required.

European Patent 1 EP0334617 describes a sweetener which comprises hollow spheroids or part spheroids of microcrystalline sucrose generally bound to crystals of sucrose and preferably containing one or more high intensity sweeteners such as sucralose. The sweetener is prepared by spray drying of sucrose syrup with simultaneous injection of an inert pressurized gas and generally contacting the sprayed syrup during the spray drying step and/or after completion of said step with crystals of sucrose and preferably incorporating the high intensity sweetener in the sucrose syrup or in the agglomeration step. A major setback of this method for production of low calorie sweetener composition which utilizes sucrose in the form of syrup as raw material, is the high power consumption and requirement of custom designed high cost equipment for spray drying process.

UK Patent GB1566821 describes a sweetening composition comprising a mixture of L-sorbose and sucrose with molar ratio of L-sorbose to sucrose within the range of 1:0.5 to 1:50. The sweetening composition is prepared by mixing granulated/powdered sucrose and L-sorbose together. A sugar-high intensity sweetener blends prepared by simple dry mixing process tends to have lower quality especially after prolonged transportation and storage when stratification of components occurs due to influence of vibration and friction.

U.S. Pat. No. 3,619,294 describes a process where Massecuite Aggregated Microcrystalline Sugar (MAMS) granules (structurally comprising cohered sugar microcrystals with internal capillary networks) are employed as a means to combine sugar with modifying agents. The disclosed process is dependent upon the internal capillary networks of the MAMS granules, which allow the applied modifying agent to impregnate the sugar granules. The disclosed process further provides an option of second treatment in which a pore closure material is applied to reduce the porosity of the surface layers of the granules, and seal off the impregnated agent from escape to or contact with the atmosphere. The drawbacks of the disclosed process include the requirement of special forms of sugar granules and additional sealing treatment.

U.S. Pat. No. 5,401,519 describes a low calorie composite sweetener by combining fructose with high intensity sweetener. The fructose particles are first covered with a non-reducing substance membrane and the high intensity sweetener is then deposited to the non-reducing substance membrane. The drawbacks of the disclosed composite sweetener include the requirement of additional bonding such as non-reducing substance membrane.

U.S. Pat. No. 6,703,057 discloses a granulated sugar product comprising a core and surface sugar layers where the core material is having higher density than the surface material. The surface material comprises substantially a second sugar, dextrins, sorbitol, mannitol, starch, cellulose, inulin, glycogen, xylitol, levoglucason or maltol (and ethyl derivative). It may also incorporate high intensity sweetener. The drawbacks of the disclosed sugar product include the requirements of another compound such as second sugar, dextrins, sorbito, mannitol, starch, cellulose, inulin, glycogen, xylitol, levoglucason, maltol or any other binding or bulking agent besides the sugar and high intensity sweetener.

U.S. Pat. No. 3,293,133 describes a process of imparting water insoluble colors to pharmaceutical solutions. According to described process the color solution is distributed onto sucrose particles to form a sucrose and coloring material blend. No adequate solutions are described to ensure even distribution of color solution on sucrose particles to produce material with maximal homogeneity. Mechanical stability of the blend obtained by described process will be insufficient.

U.S. Pat. No. 1,902,773 describes a process of protecting hygroscopic carbohydrate (fructose) with non-hygroscopic film and increasing the thickness of the film by additionally depositing non-hygroscopic carbohydrate crystals from saturated solution of non-hygroscopic carbohydrate (dextrose). Process employs a spray chamber where the hygroscopic granules are covered with film of non-hygroscopic compound by means of spraying while falling from top of the tower through spray zone where coating material is being sprayed. It has to be noted that such method of delivery of coating material cannot provide control of contact time of core particle with sprayed solution to ensure preparation of material with uniform characteristics.

SUMMARY OF THE INVENTION

An object of the present invention is to provide a commercially valuable process for producing a low calorie composite sweetener comprising sugar and high intensity sweetener, particularly sweet glycosides of *Stevia rebaudiana* Bertoni plant (hereinafter steviol glycosides), and use thereof in various food products and beverages, which overcomes the disadvantages of the related art.

The invention, in part, pertains to the granulated sugar with a specific moisture content being distributed to form a layer with specific thickness on a vibrating surface. High intensity sweetener is dissolved in a solvent mixture comprising water and alcohol to make high concentration solution which was heated up to prevent crystal formation and was dispersed on the granulated sugar by means of an air-powered pneumatic method while maintaining the granulated sugar at intensive vibration conditions. The resulted product was dried to form a low calorie sugar-high intensity sweetener blend.

The sugar-steviol glycosides blends were applied in various foods and beverages as sweetener.

The processes developed in this invention can be used also for preparation of steviol glucosides' blends with other crystalline or granulated materials, particularly sweeteners, non-limiting examples of which will include fructose, palatinose, tagatose, sugar alcohols.

It is to be understood that both the foregoing general description and the following detailed description are exemplary and explanatory and are intended to provide further explanation of the invention as claimed.

BRIEF DESCRIPTION OF THE DRAWINGS

The accompanying drawings are included to provide a further understanding of the invention. The drawings illustrate embodiments of the invention and together with the description serve to explain the principles of the embodiments of the invention.

DETAILED DESCRIPTION OF THE INVENTION

Figure 1:
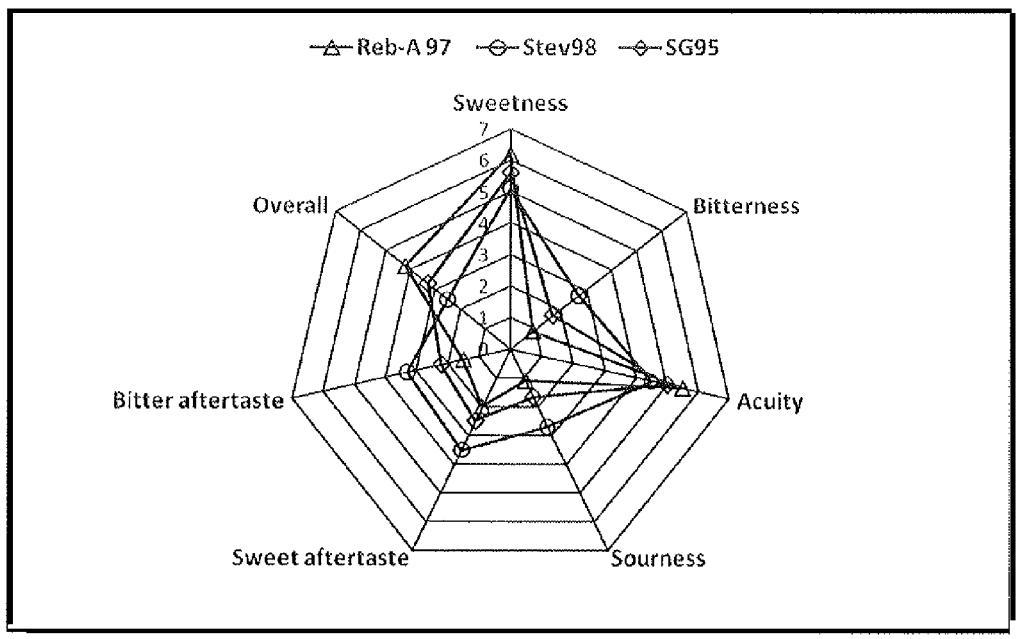
FIG. 1 shows a sensory evaluation of Reb-A 97, Stevioside 98 and SG 95.
Figure 2:
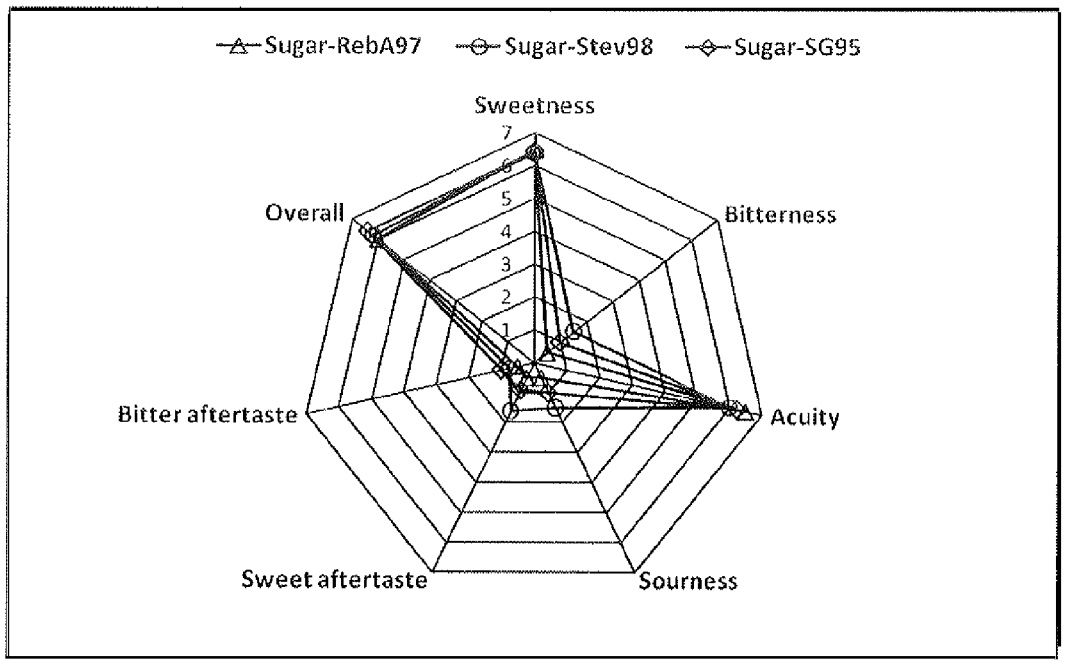
FIG. 2 shows a sensory evaluation of sugar-Reb-A 97, sugar-Stevioside 98 and sugar-SG 95 blends.

Advantages of the present invention will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The present description will use the terms and abbreviations in the sense defined as follows:

TSG content: Total Steviol Glycosides content determined by assay method described in FAO JECFA monographs 5 (2008).

High intensity sweeteners: sweeteners selected from the group consisting of stevioside, rebaudioside A, rebaudioside B, rebaudioside C, rebaudioside D, rebaudioside E, rebaudioside F, dulcoside A, dulcoside B, rubusoside, stevia, mogroside IV, siamenoside, mogroside V, Luo Han Guo sweetener, monatin and its salts (monatin SS, RR, RS, SR), glycyrrhizic acid and its salts, curculin, thaumatin, monellin, mabinlin, brazzein, hernandulcin, phyllodulcin, glycyphyllin, phloridzin, trilobatin, baiyunoside, osladin, polypodoside A, pterocaryoside A, pterocaryoside B, mukurozioside, phlomisoside I, periandrin I, abrusoside A, cyclocarioside I, and combinations thereof.

Steviol Glycosides: high intensity sweeteners selected from the group consisting of stevioside, rebaudioside A, rebaudioside B, rebaudioside C, rebaudioside D, rebaudioside E, rebaudioside F, dulcoside A, dulcoside B, and rubusoside and combinations thereof.

SG 95: mixture of Steviol Glycosides with TSG content above 95% (w/w).

Reb-A 97: high intensity sweetener with Rebaudioside A content above 97% (w/w).

Stevioside 98: high intensity sweetener with Stevioside content above 98% (w/w).

One aspect of the present invention provides a process for producing a low calorie composite sweetener comprising sugar and high intensity sweeteners. Briefly, the process comprises: adjusting the moisture content of granulate sugar to 3.0-4.0%, where the granulate sugar has a particle size of 800-1000 µm; distributing the moisturized granulate sugar on a vibrating surface to form a layer with thickness of 10-100 mm, preferably 25-35 mm; setting at vibration intensity from 1-2000 vibrations per minute (hereinafter vpm) preferably 1000-1300 vpm.

The step of adjusting moisture content of sugar granules can be accomplished by any means known to the art, for example, by contacting the sugar granules with humid air. Adjusting moisture content of sugar granules facilitates a rapid and even dispersion of the solution of high intensity sweetener on the sugar granules' surface and promotes stronger attachment between high intensity sweetener and sugar granule. The inventors of the present invention discovered that the range of the moisture content within the granulate sugar is critical for the process of producing low calorie composite sweetener and the quality of the composite sweetener produced. When the moisture content is lower than 3%, the bonding between granule surface and high intensity sweetener is not optimal; when the moisture content exceeds 4%, sugar granules tend to stick to each other, lowering the amount of high intensity sweetener bound to the sugar granules.

The preferred average particle size of granulated sugar promotes more optimal distribution of high intensity sweetener. Using material with particle size less than 800 µm at moisture levels and agitation mode employed in this invention cannot ensure sufficient mass exchange level of sugar granules and subsequent even distribution of high intensity sweetener on granules; whereas granules with size greater than 1000 µm do not provide surface area large enough hence heterogeneity of obtained blend will be higher.

Distribution of the sugar granules in a layer of specific thickness ensures the accessibility of all sugar granules to direct impact of dispersed solution of high intensity sweetener.

The vibrating surface can be a vibrating tray or vibrating conveyor. Maintaining the intensity of vibration while dispersing the solution of high intensity sweetener ensures that all available surfaces of sugar granules are able to be reached by the solution of high intensity sweetener therefore enhancing the quality uniformity of obtained sugar-high intensity sweetener blend. It also prevents the agglomeration and caking of sugar granules which often occurs in processes where other means of agitation or mixing is employed (e.g. mixing drums or blenders). Maintaining vibration intensity less than 1000 vpm or above 1300 vpm do not provide optimal mass exchange level for even distribution of high intensity sweetener.

Steviol glycoside preparation with TSG content of 95-100% (w/w) was dissolved in a solvent mixture comprising water and ethyl alcohol with ethyl alcohol content from 0.1-99.9% (v/v), preferably from 30-60% (v/v) to make steviol glycoside solution with 10-70% (w/w) preferably 30-60% (w/w) solids content.

The sugar to steviol glycoside dry weight ratio was from 50:1 to 300:1 (w/w), preferably 100:1 to 200:1 (w/w). The preferred choice of steviol glycoside was Reb-A 97, SC 95 and Stevioside 98.

The steviol glycoside aqueous alcoholic solution was heated up to 30-80° C. preferably 40-60° C. for prevention of crystal formation and was dispersed on the granulated sugar by means of pressure atomization method with pressure of compressed air at 0.01-1.0 MPa preferably 0.1-0.7 MPa over a period of 10-300 seconds, preferably 50-150 seconds while maintaining the intensity of vibration mentioned above.

Advantage of using the water-alcohol mixture for steviol glycoside dissolution compared to pure water is the increased dissolving capacity of such solvent. Most of the steviol glycosides in highly purified form have relatively low solubility in pure water. On the other hand alcohol reduces the sugar granules agglomeration possibility and tends to dry faster during the final drying step of the process. This in turn minimizes thermal degradation and color change of final product due to reduction of drying temperature and duration.

The increased temperature of the solution prevents premature crystallization of steviol glycoside, reduces the viscosity of concentrated solution and promotes partial evaporation of liquid during the dispersion of the concentrated solution onto sugar granules.

To eliminate the necessity of extensive drying process and prevent agglomeration of sugar granules a high concentration solution of high intensity sweetener is used instead of a dilute solution of high intensity sweetener.

Dispersing the solution of high intensity sweetener by means of pressure atomization allows a higher degree of dispersion even when a concentrated solution of high intensity sweetener is used. It promotes an even distribution of the high intensity sweetener on the sugar granules and minimizes agglomeration of sugar granules which often arises when the solution of high intensity sweetener is dispersed by direct addition of solution or by means of hydraulic dispersion. The amount of the solution of high intensity sweetener to be dispersed is critical depending upon the amount of the granulated sugar. In one embodiment, the amount of the solution of high intensity sweetener to be dispersed is 1-3% (w/w) of the granulated sugar.

The obtained product was dried over a period of 2-30 minutes, preferably 5-15 minutes, by means of a convective method in a drum-type drying apparatus set at a temperature of 50-85° C., preferably 60-70° C. until its moisture content was 0.01-0.5% preferably 0.05-0.1%.

The final step of drying is achievable by any drying processes known to the art.

The HPLC analysis of steviol glycosides and the obtained product was carried out using an Agilent Technologies 1200 Series (USA) equipped with Zorbax-$NH_2$ column (4.6×250 mm, 5 um) using acetonitrile-water 80:20, (v/v) mobile phase and UV detector at 210 nm as described in FAO JECFA Monographs 5 (2008).

The physico-chemical characteristics of obtained products were compared with a control sample produced by conventional method. It was shown that for all tested characteristics the samples prepared according to the process of this invention possess clear advantage compared with control sample.

The organoleptic test was carried out with 30 previously trained panel members. The test was carried out on water solutions of sugar-steviol glycoside blends with, Reb-A 97, Stevioside 98 and SG 95, as well as on same sweeteners used "as is". It was observed that in all cases sugar-steviol glycoside blends have more acceptable taste profile compared to case when the same sweeteners are used "as is" without blending with other sweeteners. The sugar-Reb-A 97 blend had the lowest score for bitterness, while Stevioside 98 used "as is" was the most bitter compared to the other samples. For overall acceptability, sugar-Reb-A 97 blend had the highest score followed by SG 95, and Stevioside 98.

The obtained low-calorie composite sweetener can be favorably used for seasoning various food products (for instance, soy sauce, soy sauce powder, soy paste, soy paste powder, dressings, mayonnaise, vinegar, powdered vinegar, bakery products and confectioneries, frozen-desserts, meat products, fish-meat products, potato salad, bottled and canned foods, fruit and vegetables) in intact or mixed forms with other sweeteners, such as corn syrup, glucose, maltose, sucrose, lactose, aspartame, saccharin, sugar alcohols, organic and amino acids, flavors and/or coloring agents.

The products are favorably usable as low-calorie sweetener in exemplary applications including low-cariogenic food products such as confectioneries including chewing gum, chocolate, biscuits, cookies, toffee and candy. Additional applications include soft drinks such as coffee, cocoa, juice, carbonated drinks, sour milk beverage, yogurt drinks and alcoholic drinks, such as brandy, whisky, vodka and wine. In addition to the above-described uses, the sweeteners are usable for sweetening drugs and cosmetics.

The following examples illustrate preferred embodiments of the invention.

EXAMPLE 1

Sugar Based Sweetener with Reb-A 97

1490 g of granulated sugar with average particle size 800-1000 μm and moisture content adjusted to 3.9% was distributed to form a layer with thickness of 30 mm on a vibrating tray. 10.03 g Reb-A 97 (containing stevioside 0.31%, rebaudioside C 0.21%, rebaudioside A 98.56%, rebaudioside B 0.22%) was dissolved in 15.04 g of solvent mixture containing 4 volumes of water per 1 volume of ethyl alcohol to make rebaudioside A 40% (w/w) solution. The solution was heated up to 40° C. for prevention of crystal formation and was dispersed on the granulated sugar by means of an air-powered pneumatic method with pressure of compressed air at 0.1 MPa over a period of 100 seconds while maintaining the intensity of vibration at 1200 vpm. The granulated sugar was dried over a period of 10 minutes by means of a convective method in a drum-type drying apparatus set at a temperature of 65° C. until its moisture content was 0.08%.

The sweetener produced had homogenous and intact structure of crystal sugar and had identical taste profile as sucrose with sweetness power 3 times higher than sugar.

EXAMPLE 2

Sugar Based Sweetener with Stevioside 98

1488 g of granulated sugar with average particle size 800-1000 μm and moisture content adjusted to 3.4% was distributed to form a layer with thickness of 30 mm on a vibrating tray. 12.05 g stevioside 98 (containing stevioside 98.51%, rebaudioside C 0.31%, rebaudioside A 0.26%, steviolbioside 0.22%) was dissolved in 18.07 g of solvent mixture containing 4 volumes of water per 1 volume of ethyl alcohol to make stevioside 40% (w/w) solution. The solution was heated up to 40° C. for prevention of crystal formation and was dispersed on the granulated sugar by means of an air-powered pneumatic method with pressure of compressed air at 0.1 MPa over a period of 100 seconds while maintaining the intensity of vibration at 1200 vpm. The granulated sugar was dried over a period of 10 minutes by means of a convective method in a drum-type drying apparatus set at a temperature of 65° C. until its moisture content was 0.09%.

The sweetener produced had homogenous and intact structure of crystal sugar and had almost identical taste profile as sucrose with sweetness power 3 times higher than sugar.

EXAMPLE 3

Sugar Based Sweetener with SG 95

1488 g of granulated sugar with average particle size 800-1000 μm and moisture content adjusted to 3.4% was distributed to form a layer with thickness of 30 mm on a vibrating tray. 11.58 g SG 95 (containing rubusoside 0.21%, dulcoside A 0.39%, stevioside 30.31%, rebaudioside C 11.85%, rebaudioside A 51.56%, steviolbioside 0.23%, rebaudioside B 1.01%) was dissolved in 17.37 g of solvent mixture containing 4 volumes of water per 1 volume of ethyl alcohol to make 40% (w/w) solution. The solution was heated up to 40° C. for prevention of crystal formation and was dispersed on the granulated sugar by means of an air-powered pneumatic method with pressure of compressed air at 0.1 MPa over a period of 100 seconds while maintaining the intensity of vibration at 1200 vpm. The granulated sugar was dried over a period of 10 minutes by means of a convective method in a drum-type drying apparatus set at a temperature of 65° C. until its moisture content was 0.05%.

The sweetener produced had homogenous and intact structure of crystal sugar and had identical taste profile as sucrose with sweetness power 3 times higher than sugar.

EXAMPLE 4

Control Sugar Based Sweetener with Steviol Glycoside

Three batches of sugar based sweeteners were made using Stevioside 98, Reb-A 97 and SG 95. 1490 g of granulated sugar was placed in rotary drum mixer. 10.03 g of Reb-A 97, 12.05 g of Stevioside 98 and 11.58 g of SG 95 were dissolved in enough amount of water to make saturated solutions at 40° C. The solutions were dispersed on the granulated sugar by means of an air-powered pneumatic method while rotating the drum mixer. The obtained mixtures were dried in a drum-type drying apparatus set at a temperature of 65° C. until moisture content less than 0.1%.

Produced sweeteners were compared with sweeteners prepared as per Examples 1, 2 and 3.

To evaluate the stratification of components due to mechanical impact the sweeteners were placed in air tight containers and placed on a vibrating platform set at 2000 vpm during 24 hours. Upon completion 3 samples were withdrawn from each container (top, middle bottom) and analyzed via HPLC to determine the consistency of steviol glycoside content in all levels. Each sample was evaluated also to determine its sweetness compared to intact sugar.

Additionally the sweeteners were analyzed on a 60 mesh test sieve to evaluate the amount of steviol glycoside "chipping off" from the surface of sugar granules. The results of evaluation are summarized in TABLE 1.

TABLE 1

| Parameter | Invention samples | | | Control samples | | |
|---|---|---|---|---|---|---|
| | Reb-A 97 | Stevioside 98 | SG 95 | Reb-A 97 | Stevioside 98 | SG 95 |
| Appearance | Same as granulated sugar | | | Similar to granulated sugar | | |
| Steviol glycoside content, % (w/w) | | | | | | |
| Top layer | 0.64 | 0.78 | 0.75 | 0.38 | 0.36 | 0.52 |
| Middle layer | 0.66 | 0.79 | 0.75 | 0.54 | 0.61 | 0.65 |
| Bottom layer | 0.66 | 0.80 | 0.77 | 1.05 | 1.40 | 1.11 |
| Sweetness, fold sugar sweetness | | | | | | |
| Top layer | 3 | 3 | 3 | 2 | 2 | 2 |
| Middle layer | 3 | 3 | 3 | 2.5 | 2.5 | 2.5 |
| Bottom layer | 3 | 3 | 3 | 4 | 4.5 | 4 |
| Steviol glycoside recovered after sieve, % from applied amount | 1.1 | 1.3 | 0.9 | 21.2 | 25.6 | 15.3 |

EXAMPLE 5

Low-Calorie Orange Juice Drink

Orange concentrate (35%), citric acid (0.38%), ascorbic acid (0.05%), sodium benzoate (0.02%), orange red color (0.01%), orange flavor (0.20%), and low-calorie sweetener compositions (5.0%) prepared as per examples 1, 2 and 3 were blended and dissolved completely in the water (up to 100%) and pasteurized. The sensory evaluation of the samples is summarized in the TABLE 2. The data shows that best results were obtained for sweetener composition with Reb-A 97.

TABLE 2

| Sample | Flavor | Comments | |
|---|---|---|---|
| | | Aftertaste | Mouth feel |
| Stevioside 98 | Sweet, rounded and balanced Flavor, taste similar to sucrose | Almost no any bitterness | Acceptable |
| SG 95 | Sweet, rounded and balanced Flavor, taste similar to | No any bitterness | Full |

TABLE 2-continued

| | Comments | | |
|---|---|---|---|
| Sample | Flavor | Aftertaste | Mouth feel |
| Reb-A 97 | High quality of sweetness, pleasant, taste similar to sucrose, balanced flavor | Clean, no unpleasant aftertaste | Quite full | sucrose

Similarly juices from other fruits, such as apple, lemon, apricot, cherry, pineapple, etc can be prepared.

EXAMPLE 6

Low-Calorie Carbonated Lemon-Flavored Beverage

The formula for the beverage was as below:

| Ingredients | Quantity |
|---|---|
| Sugar-steviol glycosides blend | 43.3 kg |
| Citric acid | 2.5 kg |
| Green tea extract | 25.0 kg |
| Salt | 0.3 kg |
| Lemon tincture | 10.0 L |
| Juniper tincture | 8.0 L |
| Sodium benzoate | 0.17 |
| Carbonated water | up to 1000 L |

Sensory and physicochemical characteristics of the drink are presented in the TABLE 3.

The drinks with highly purified Rebaudioside A and Stevioside were superior with an excellent flavor and taste.

TABLE 3

| | Sugar-steviol glycosides blend | | |
|---|---|---|---|
| Characteristics | Stevioside 98 | SG 95 | Reb-A 97 |
| Appearance | Transparent liquid, free of sediment and foreign impurities. | Transparent liquid, free of sediment and foreign impurities. | Transparent liquid, free of sediment and foreign impurities. |
| Color | From light yellow up to yellow | From light yellow up to yellow | From light yellow up to yellow |
| Taste | Sour-sweet, expression of sweetness is rapid. The taste is satisfactory. | Sour-sweet, no any bitterness, expression of sweetness is rapid. | Sour-sweet, expression of sweetness is rapid. |

EXAMPLE 7

Low-Calorie Carbonated Drink

The formula for the beverage was as below:

| Ingredients | Quantity, % |
|---|---|
| Cola flavor | 0.340 |
| Phosphoric acid (85%) | 0.100 |
| Sodium citrate | 0.310 |
| Sodium benzoate | 0.018 |
| Citric acid | 0.018 |
| Sugar-steviol glycosides blend | 2.500 |
| Carbonated water | to 100 |

The beverages prepared with different sweeteners were given to 30 judges for comparison.

TABLE 4 shows the results.

TABLE 4

| | Number of panelists (out of 30) | | |
|---|---|---|---|
| Characteristics | Stevioside 98 | SG 95 | Reb-A 97 |
| Bitter taste | 1 | 0 | 0 |
| Astringent taste | 1 | 0 | 0 |
| Aftertaste | 1 | 0 | 0 |
| Quality of sweet taste | 27 (clean) | 29 (clean) | 30 (clean) |
| Overall evaluation | 29 (satisfactory) | 30 (satisfactory) | 30 (satisfactory) |

The above results show that all the prepared beverages possess good organoleptic characteristics.

EXAMPLE 8

Chocolate

A composition containing 30 kg of cacao liquor, 11.5 kg of cacao butter, 14 kg of milk powder, 33.67 kg of sorbitol, 0.1 kg of salt, and 10.43 kg of sweetener prepared according to the EXAMPLES 1, 2 and 3, was kneaded sufficiently, and the mixture was then placed in a refiner to reduce its particle size for 24 hours. Thereafter, the content was transferred into a conche, 300 grams of lecithin was added, and the composition was kneaded at 50° C. for 48 hours. Then, the content was placed in a shaping apparatus, and solidified.

The products were low-cariogenic and low-calorie chocolate with excellent texture. Also, the organoleptic test carried out with 30 panelists revealed no lingering after-taste.

EXAMPLE 9

Ice-Cream 1.50 kg of whole milk were heated to 45° C., and 300 grams of milk cream, 50 grams of tagatose, 28.75 grams of sorbitol, 6 grams of carrageenan as a stabilizer, 3 grams of polysorbate-80 as an emulsifier, and 112.25 gram of sweetener prepared according to the EXAMPLES 1, 2 or 3, were added into the milk and was stirred until the ingredients completely dissolved. The mixture then was pasteurized at a temperature of 80° C. for 25 seconds. The homogenization of the obtained mixture was carried out at a pressure of 800 bars and the samples were kept at a temperature of 4° C. for 24 hours to complete the aging process. Vanilla flavor (1.0% of the mixture weight) and coloring (0.025% of the mixture weight) are added into the mixture after aging. The mixture was then transferred to ice cream maker to produce ice cream automatically. Samples of ice creams produced were transferred to seal containers and were kept in the freezer at a temperature of −18° C.

Organoleptic test carried out with 30 panelists. The application of sweeteners does not affect the physicochemical properties of ice cream, as well as the overall attributes of color, smoothness, surface texture, air cell, vanilla aroma intensity, vanilla taste, chalkiness, iciness and melting rate.

EXAMPLE 10

Yogurt

In 5 kg of defatted milk, 333.2 grams of sweetener, prepared according to EXAMPLES 1, 2 and 3, were dissolved. After pasteurizing at 82° C. for 20 minutes, the milk was cooled to 40° C. A starter in amount of 150 grams was added and the mixture was incubated at 37° C. for 6 hours. Then, the fermented mass was maintained at 10-15° C. for 12 hours.

The product is a low-calorie and low-cariogenic yoghurt without foreign taste and odor.

EXAMPLE 11

Tooth Paste

A tooth paste was prepared by kneading a composition comprising of calcium phosphate, 45.0%; carboxymethylcellulose, 1.5%; carrageenan, 0.5%; glycerol, 18.0%; polyoxyethylene sorbitan mono-ester, 2.0%; beta-cyclodextrin, 1.5%; sodium laurylsarcosinate, 0.2%; flavoring, 1.0%; preservative, 0.1%; sweetener, obtained according to the EXAMPLE 1, 2 or 3, 16.6%; and water to 100%, by usual way. The product possesses good foaming and cleaning abilities with appropriate sweetness.

EXAMPLE 12

Soy Sauce 5.6 g of sweetener, obtained according to the EXAMPLE 1, 2 or 3 was added to 1000 mL of soy sauce and mixed homogenously. The products had an excellent taste and texture.

EXAMPLE 13

Bread 1 kg of wheat flour, 11.65 grams of fructooligosaccharide syrup, 80 grams of margarine, 20 grams of salt, 20 grams of yeasts, and 25.98 grams of sweetener, obtained according to the EXAMPLE 1, 2 or 3 were placed into the blender and mixed well. 600 mL of water was poured into the mixture and kneaded sufficiently. At the completion of the kneading process, the dough was shaped and raised for 30 to 45 minutes. The ready dough was placed in oven and baked for 45 minutes. Bread samples had creamy white color, and smooth texture.

EXAMPLE 14

Diet Cookies

Flour (50.0%), margarine (30.0%), whole milk (1.0%), salt (0.2%), baking powder (0.15%), vanillin (0.1%), sweetener, obtained according to the EXAMPLE 1, 2 or 3 (18.55%), were kneaded well in dough-mixing machine. After molding of the dough the cookies were baked at 200° C. for 15 minutes.

The product is a low-caloric diet cookie with excellent taste and appropriate sweetness.

EXAMPLE 15

Cake 123 g of hen eggs, 1.77 g of sugar, 345 g of sorbitol liquid, 2.0 g of sucrose fatty acid ester, 43.58 g of sweetener, obtained according to the EXAMPLE 1, 2 or 3 was mixed with 100 g of wheat flour and 200 g of water in order to prepare a cake according to a conventional method. The product had an excellent taste with an optimal sweet flavor.

It is to be understood that the foregoing descriptions and specific embodiments shown herein are merely illustrative of the best mode of the invention and the principles thereof, and that modifications and additions may be easily made by those skilled in the art without departing for the spirit and scope of the invention, which is therefore understood to be limited only by the scope of the appended claims.

We claim:
1. A low calorie composite sweetener comprising:
a high intensity sweetener; and
a granulate sugar;
wherein the surface of the granulate sugar is coated with a layer of the high intensity sweetener; wherein the low calorie composite sweetener has a moisture content of 0.01-0.5 w/w %; and wherein the amount of the coated layer of the high intensity sweetener on the surfaces of the granulate sugar is in the range of 0.5-1 w/w %.
2. The low calorie composite sweetener of claim 1, wherein the composite sweetener is produced by the following steps:
adjusting the moisture content of granulate sugar to 3.0 to 4.0%;
distributing the moisturized granulate sugar on a vibrating surface to form a layer with thickness or 10-100 mm;
setting at vibration intensity from 1-2000 vibrations per minute (hereinafter vpm);
preparing a solution of high intensity sweetener in aqueous alcohol;
dispersing the solution of high intensity sweetener onto the moisturized granulate sugar while maintaining the vibration intensity of the vibrating surface; and
drying the granulate sugar to form the low calorie composite sweetener.
3. The low calorie composite sweetener of claim 1, wherein the high intensity sweetener is selected from the group consisting of stevioside, rebaudioside A, rebaudioside B, rebaudioside C, rebaudioside D, rebaudioside E, rebaudioside F, dulcoside A, dulcoside B, rubusoside, steviol glycosides, stevia, siamenoside, mogroside IV, mogroside V, Luo Han Guo sweetener, monatin and its salts (monatin SS, RR, RS, SR), glycyrrhizic acid and its salts, curculin, thaumatin, monellin, niabinlin, brazzein, hernandulein, phyllodulcin, glycyphyllin, phloridzin, trilobatin, baiyunoside, osladin, polypodoside A, pterocaryoside A, pterocaryoside B, mukurozioside, phlomisoside I, periandrin I, abrusoside A, cyclocarioside I, and combinations thereof.
4. A low calorie product comprising a low calorie composite sweetener, wherein the low calorie composite sweetener comprises:
a high intensity sweetener; and
a granulate sugar;
wherein the surface of the granulate sugar is coated with a layer of the high intensity sweetener; wherein the low calorie composite sweetener has a moisture content of 0.01-0.5 w/w %; and wherein the amount of the coated layer of the high intensity sweetener on the surfaces of the granulate sugar is in the range of 0.5-1 w/w %.

5. The low calorie product of claim 4, wherein the high intensity sweetener is selected from the group consisting of stevioside, rebaudioside A, rebaudioside B, rebaudioside C, rebaudioside D, rebaudioside F, rebaudioside F, dulcoside A, dulcoside B, rubusoside, steviol glycosides, stevia, siamenoside, mogroside IV, mogroside V, Luo Han Guo sweetener, monatin and its salts (monatin SS, RR, RS, SR), glycyrrhizic acid and its salts, curculin, thaumatin, monellin, mabinlin, brazzein, hernandulcin, phyllodulcin, glycyphyllin, phloridzin, trilobatin, baiyunoside, osladin, polypodoside pterocaryoside A, pterocaryoside B, mukurozioside, phlomisoside I, periandrin I, abrusoside A, cyclocarioside I, and combinations thereof.

6. The low calorie product of claim 4, wherein the product includes low calorie food, soft drink, milk product, alcoholic drink, drug, and cosmetics.

\* \* \* \* \*

UNITED STATES PATENT AND TRADEMARK OFFICE
CERTIFICATE OF CORRECTION

PATENT NO. : 8,591,980 B2
APPLICATION NO. : 13/684255
DATED : November 26, 2013
INVENTOR(S) : Avetik Markosyan and Siddhartha Purkayastha It is certified that error appears in the above-identified patent and that said Letters Patent is hereby corrected as shown below:

In the Claims:

| | | |
|---|---|---|
| Claim 3 | (Column 12, Line 52), | "niabinlin" should be "mabinlin" |
| Claim 3 | (Column 12, Line 52), | "hernandulein" should be "hernandulcin" |
| Claim 5 | (Column 13, Line 4), | 1st occurrence of "rebaudioside F" should be "rebaudioside E" |
| Claim 5 | (Column 13, Line 10), | "polypodoside" should be "polypodoside A," |

Signed and Sealed this
Fourth Day of March, 2014

Michelle K. Lee
*Deputy Director of the United States Patent and Trademark Office*